US006425852B1

(12) United States Patent
Epstein et al.

(10) Patent No.: US 6,425,852 B1
(45) Date of Patent: *Jul. 30, 2002

(54) APPARATUS AND METHOD FOR TRANSCRANIAL MAGNETIC BRAIN STIMULATION, INCLUDING THE TREATMENT OF DEPRESSION AND THE LOCALIZATION AND CHARACTERIZATION OF SPEECH ARREST

(75) Inventors: Charles M. Epstein, Atlanta, GA (US); Kent R. Davey, New Smyrna Beach, FL (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/484,820

(22) Filed: Jan. 18, 2000

Related U.S. Application Data (63) Continuation of application No. 09/125,646, filed as application No. PCT/US97/14826 on Aug. 15, 1997, now Pat. No. 6,132,361, which is a continuation-in-part of application No. 08/345,572, filed on Nov. 28, 1994, now Pat. No. 5,725,471.
(60) Provisional application No. 60/023,421, filed on Aug. 15, 1996.

(51) Int. Cl.$^7$ .............................. A61N 2/00; A61B 17/52
(52) U.S. Cl. ........................................... 600/13; 600/15
(58) Field of Search ...................... 600/9–15; 607/48–52

(56) References Cited

U.S. PATENT DOCUMENTS

| 4,940,453 A |   | 7/1990  | Cadwell      |         |
|-------------|---|---------|--------------|---------|
| 5,116,304 A |   | 5/1992  | Cadwell      |         |
| 5,441,495 A |   | 8/1995  | Liboff et al.|         |
| 5,725,471 A | * | 3/1998  | Davey et al. | 600/13  |
| 6,132,361 A | * | 10/2000 | Epstein et al.| 600/13 |

FOREIGN PATENT DOCUMENTS

RU   2008946   3/1994

OTHER PUBLICATIONS

C.M. Epstein et al., Localizing the Site of Magnetic Brain Stimulation in Humans, Neurology, vol. 40, pp. 666–670, 1990.
S.M. Hersch et al., Biological Consequence of Transcranial Magnetic Stimulation on the Mouse, Society for Neuroscience Abstracts, vol. 16, 551.7, 1990.
J.D. Weissman et al., Magnetic Brain Stimulation and Brain Size: Relevance to Animal Studies, vol. 85, p. 215–219, 1992.
P.P. Brodak et al., Magnetic Stimulation of the Sacral Roots, Neurourology and Urodynamics, vol. 12, pp. 533–540, 1993.
T. Kujirai et al., The Effect of Transcranial Magnetic Stimulation on Median Nerve Somatosensory Evoked Potentials, Electroencephalography and Clinical Neurophysiology, vol. 89, pp. 227–234, 1993.
Y. Omura et al., Basic Electrical Parameters for Safe and Effective Therapeutics . . . , Accupuncture and Electro–Therapeutics Res., Int. J., vol. 12, pp. 201–225, 1987.
R.W. Gulch and O. Lutz, Influnece of Strong Magnetic Fields on Heart Muscle Construction, Phys. Med. Biol., vol. 31, No. 7, pp. 763–767, 1986.
J. Bucking et. al., The Influence of a Strong Magnetic Field on Muscular Contraction, (Rad.?) and Environ. Biophys., vol. 11, pp. 79–85, 1974.

\* cited by examiner

*Primary Examiner*—John P. Lacyk
(74) *Attorney, Agent, or Firm*—Levisohn, Lerner, Berger & Langsam (57) ABSTRACT

An apparatus and method for transcranial magnetic brain stimulation. The apparatus allows transcranial stimulation at higher power efficiency and lower heat generation than prior available magnetic stimulator coils without an iron core. Use of the apparatus allows an improved method for active localization of language function. The device can also be used in rapid rate transcranial magnetic stimulation for the treatment of depression.

26 Claims, 8 Drawing Sheets

TABLE: 1
ANTIDEPRESSANT DOSAGES RECEIVED
PRIOR TO rTMS

| MEDICATION DOSAGES | # OF PATIENTS TAKING |
|---|---|
| PAXIL ≥ 20 mg | 15 |
| PROZAC ≥ 20 mg | 6 |
| ZOLOFT ≥ 50 mg | 4 |
| TRAZADONE ≥ 200 mg | 1 |
| EFFEXOR ≥ 150 mg | 1 |
| WELLBUTRIN ≥ 300 mg | 3 |

TABLE: 2
AGE AND SEX OF RESPONDERS & NON-RESPONDERS

| AGE | RESPONDERS | NON-RESPONDERS |
|---|---|---|
| MEAN | 35 | 46 |
| RANGE | 32-62 | 22-64 |
| MALES | 7 | 7 |
| FEMALES | 9 | 5 |

TABLE: 3
DIAGNOSIS OF RESPONDERS AN NON-RESPONDERS

| DIAGNOSIS | RESPONDERS | NON-RESPONDERS |
|---|---|---|
| MAJOR DEPRESSION UNIPOLAR RECURRENT | 14 | 11 |
| MAJOR DEPRESSION RECURRENT WITH PSYCHOTIC FEATURES | 1 | 1 |
| BIPOLAR DISORDER | 2 | 1 |

APPARATUS AND METHOD FOR TRANSCRANIAL MAGNETIC BRAIN STIMULATION, INCLUDING THE TREATMENT OF DEPRESSION AND THE LOCALIZATION AND CHARACTERIZATION OF SPEECH ARREST

RELATED APPLICATIONS

This application is a continuation of U.S. application Ser. No. 09/125,646, filed Mar. 15, 1999 now U.S. Pat. No. 6,132,361, which claims the priority of 371PCT Application Ser. No. PCT/US97/14826, filed Aug. 15, 1997, which claims priority of U.S. Provisional Application Ser. No. 60/023,421, filed Aug. 15, 1996, and which is a continuation-in-part of U.S. patent application Ser. No. 08/345,572 filed Nov. 28, 1994 (issued as U.S. Pat. No. 5,725,471 on Mar. 10, 1998), the disclosures of which are incorporated herein by reference.

FIELD OF THE INVENTION

The present invention relates to an apparatus for transcranial magnetic brain stimulation. The invention also relates to methods for localizing and characterizing speech arrest, and for treatment of depression using transcranial magnetic stimulation.

BACKGROUND OF THE INVENTION

The Magnetic Stimulator Apparatus

Magnetic stimulation of neurons has been heavily investigated over the last decade. Almost all magnetic stimulation work has been done in vivo. The bulk of the magnetic stimulation work has been in the area of brain stimulation.

Cohen has been a rather large contributor to this field of research (See e.g., T. Kujirai, M. Sato, J. Rothwell, and L. G. Cohen, "The Effects of Transcranial Magnetic Stimulation on Median Nerve Somatosensory Evoked Potentials", *Journal of Clinical Neurophysiology and Electro Encephalography*, Vol. 89, No. 4, 1993, pps. 227–234, the disclosure of which is fully incorporated herein by reference.) This work has been accompanied by various other research efforts including that of Davey, et al. and that of Epstein (See, K. R. Davey, C. H. Cheng, C. M. Epstein "An Alloy—Core Electromagnet for Transcranial Brain Stimulation", *Journal of Clinical Neurophysiology*, Volume 6, Number 4, 1989; and, Charles Epstein, Daniel Schwartzberg, Kent Davey, and David Sudderth, "Localizing the Site of Magnetic Brain Stimulation in Humans", *Neurology*, Volume 40, April 1990, pps. 666–670, the disclosures of which are fully incorporated herein by reference).

Generally, the magnetic stimulation research has used air type coils in their stimulators. These coils are so named due to the fact that they lack a magnetic core. A well known producer of such coils is Cadwell, which produces a variety of different models. One of the goals of the present inventors has been to provide magnetic stimulator devices for use in a variety of applications, which are improvements over the devices previously used in the art. In our prior issued U.S. Pat. No. 5,725,471, filed Nov. 28, 1994 and issued Mar. 10, 1998, which is the parent to the present application (the disclosure of which is fully incorporated herein by reference), a variety of such devices were disclosed for the use in peripheral nerve stimulation. Accordingly, it is an object of the present inventors herein to provide further devices for use in central nervous system stimulation in general, and transcranial brain stimulation in particular.

The Treatment of Depression

Transcranial magnetic stimulation is known to non-invasively alter the function of the cerebral cortex. (See e.g., George M S, Wassermann E M, Post R M, Transcranial magnetic stimulation: A neuropsychiatric tool for the 21st century, *J. Neuropsychiatry*, 1996; 8: 373–382, the disclosure of which is fully incorporated herein by reference). The magnetic fields used are generally generated by large, rapidly-changing currents passing through a wire coil on the scalp. Two recent studies have suggested that rapid rate transcranial magnetic stimulation (rTMS) may be used for exploring the functional neuroanatomy of emotions: healthy volunteers who received left pre-frontal stimulation reported an increase in self-rated sadness, while, in contrast, right pre-frontal stimulation caused an increase in happiness. (See, Pascual-Leone A., Catala M D, Pascual A P, Lateralized effect of rapid rate transcranial magnetic stimulation of the prefrontal cortex on mood, *Neurology*, 1996; 46: 499–502; and, George M S, Wasserman E M, Williams W., et al., Changes in mood and hormone levels after rapid-rate transcranial magnetic stimulation of the prefrontal cortex, *J. Neuropsychiatry Clin. Neurosci.* 1996; 8: 172–180, the disclosures of which are fully incorporated herein by reference.)

Other reports have begun to delineate the therapeutic use of rTMS in depression. The earliest such studies used round, non-focal coils centered at the cranial vertex, with stimulation rates well under 1 Hertz (Hz). Results were promising but not always statistically significant. (See, Hoflich G., Kasper S. Hufnagel A. et al., Application of transcranial magnetic stimulation in treatment of drug-resistant major depression: a report of two cases, *Human Psychopharmacology*, 1993; 8: 361–365; Grisaru N., Yarovslavsky U., Abarbanel J., et al., Transcranial magnetic stimulation in depression and schizophrenia, *Eur. Neuropsychopharmacol.* 1994; 4: 287–288; and, Kilbinger H M, Hofllich G., Hufnagel A., et al., Transcranial magnetic stimulation (TMS) in the treatment of major depression: A pilot study, *Human Psychopharmacology*, 1995; 10: 305–310, the disclosures of which are fully incorporated herein by reference.)

Subsequently, George et al., described striking improvement in some depressed patients from treatment with rTMS over the left pre-frontal cortex. (See, George M S, Wasserman E M, Williams W A, et al., Daily repetitive transcranial magnetic stimulation (rTMS) improves mood in depression, *NeuroReport*, 1995; 6: 1853–1856; and, George M S, Wasserman E M, Williams W E, Kimbrell T A, Little J T, Hallett M., Post R M, Daily left prefrontal rTMS improves mood in outpatient depression: a double blind placebo-controlled crossover trial, *Am. J. Psychaitry*, 1997 (in press), the disclosures of which are fully incorporated herein by reference). The largest such study to date was reported by Pascual-Leone et al., who used a five-month double blind placebo-controlled cross over design with five different treatment conditions. (See, Pascual-Leone A., Rubio B., Pallardo F. Catala M D, Rapid-rate transcranial magnetic stimulation of left dorsolateral prefrontal cortex in drug-resistant depression, *The Lancet*, 1996; 348: 233–237, the disclosure of which is fully incorporated herein by reference.) Left pre-frontal rTMS was uniquely effective in 11 of 17 young (less than 60 years of age) psychotically depressed and medication resistant patients.

Accordingly, further to the work which has been done thus far in this field, it is also a goal of the present inventors to provide improved apparatus and methods for transcranial magnetic stimulation, and for the treatment of depression using such stimulation, as described more fully hereafter.

The Localization of Speech Arrest

With respect to the methods previously used for the localization of speech arrest, active localization of language function has traditionally been possible only with invasive procedures. The dominant hemisphere can be determined using the intracarotid amobarbital or Wada test. Cortical areas critical to language can be mapped using electrocorticography in the operating room, (See e.g. Penfield, 1950, cited below) or extra-operatively through electrode grids implanted in the subdural space. (See e.g. Lesser, 1987, cited below). The Wada test and electrocorticography have contributed greatly to our current understanding of language organization. However, because of their complexity and potential morbidity, these techniques are confined almost entirely to patients undergoing surgery for intractable epilepsy.

In the past decade, positron emission tomography and functional magnetic resonance imaging have shown promising results for language localization. But these newer imaging technologies requite complex and expensive equipment, and have other limitations in the form of poor temporal resolution or a restricted test environment. The correlation between the degree of metabolic change in different brain areas and their importance for a given cognitive task remains unknown. (See e.g., Ojemann, cited below).

At least four groups have reported lateralized speech arrest using rapid-rate transcranial magnetic brain stimulation (rTMS) in epilepsy patients. (See e.g., Pascual-Leone, 1991, Michelucci, 1994, Jennum, 1994, and Epstein, 1996, cited below). The results showed a high correlation with the Wada test, but sensitivity in the two largest series was only 50–67% (See, e.g., Jennum, 1994, and Michelucci, 1994, cited below). Most of these studies used large circular magnetic coils, along with stimulus parameters that may carry a risk of inducing seizures. (See, e.g. Pascual-Leone, 1993, cited below). Thus, the initial rTMS techniques were not optimal for detailed localization or for studies involving normal subjects.

Consequently, further to the work which has previously been done, it is also a goal of the present inventors to provide improved apparatus and methods for localization and characterization of brain function. As described hereafter, we recently described modifications of rTMS that produce lateralized speech arrest with reduced discomfort, a repetition rate as low as four Hertz, and a combination of stimulus parameters that comply with recent recommendations for safety in rTMS (See also, Epstein C M, Lah J J, Meador K, Weissman J D, Gaitain L E, Dihenia B, Optimum stimulus parameters for lateralized suppression of speech with magnetic brain stimulation, *Neurology*, 47: 1590–1593 (December 1996), the disclosure of which is fully incorporated herein by reference). The technique is useful for detailed studies of magnetic speech arrest in normal individuals.

SUMMARY OF THE INVENTION

An object of the present invention is to provide an improved apparatus for transcranial magnetic brain stimulation.

A further object of the present invention is to provide an improved method for characterizing and localizing brain function.

A further object of the present invention is to provide an improved method for characterizing and localizing speech arrest.

A further object of the present invention is to provide an improved method for treatment of depression.

As disclosed more fully hereafter, an apparatus is described for use in transcranial brain stimulation. The apparatus is designed to produce a focussed magnetic field which can be directed at sites on the brain of interest or importance. The device consists of at least one, but preferably four magnetic cores. The cores are preferably constructed of a ferromagnetic material. The cores can have an outer diameter between approximately 2 and 7 inches, and an inner diameter between approximately 0.2 and 1.5 inches. The material of the cores has a magnetic saturation of at least 0.5 Tesla, and preferably at least 1.5 Tesla, or even 2.0 Tesla or higher. In the preferred embodiment, the core conforms in construction to the shape of the head to improve its efficacy. A visualization and location port is included to assist with the precision placement of the core on the head, and to assist with exact marking of the stimulator's position.

Using the described apparatus and method, an optimized technique for transcranial magnetic brain stimulation is provided which has a variety of useful applications. For example, the present apparatus and method can be employed for brain stimulation in a therapeutic protocol for the treatment of depression. In addition, the apparatus and method can be used for the localization and characterization of brain function. For example, detailed anatomic localization of speech arrest and effects on other language function can be studied. The invention therefore provides devices and methods for non-invasive stimulation and treatment of the brain, and for studying and characterizing brain function, which are improvements over the procedures of the prior art.

Using the apparatus and technique on four normal right-handed volunteers, to study speech arrest for example, it was determined that all were dominant for magnetic speech arrest over the left hemisphere. While subjects counted aloud, points of speech arrest were mapped on a one-centimeter grid over the left frontal region. Compound motor action potentials from muscles in the right face and hand were mapped onto the same grid. Subjects were then tested in reading, writing, comprehension, repetition, naming, spontaneous singing, and oral praxis during magnetic stimulation. Finally, mean positions for speech arrest and muscle activation were identified on three dimensional MRI.

All of the subjects tested using the present technique had complete, lateralized arrest of counting and reading with magnet stimulation over the left posterior-inferior frontal region. Writing with the dominant hand, comprehension, repetition, visual confrontation naming, oral praxis, and singing were relatively or entirely spared, with rare aphasic errors. In two subjects, melody was abolished from singing during stimulation over the right hemisphere. In all four subjects, the region of speech arrest was highly congruous with the region where stimulation produced movement of the right face, and overlay the caudal portion of the precentral gyrus. This constellation of behavioral and anatomic findings is similar to that found in aphemia, and supports a modular theory of language organization in the left hemisphere.

In patients with refractory depression, the stimulator of the present invention was used to stimulate the brain with magnetic pulses using rapid rate transcranial magnetic stimulation over the left prefrontal region of the brain. In a group of 32 patients aged 22–64, all Hamilton Depression (Ham-D) scores were above 20 prior to treatment. Twenty-eight (28) patients completed treatment: average Ham-D scores fell from thirty one (31) to fifteen (15), and individual scores fell to less than ten (10) in fourteen (14) out of twenty-eight (28) of the subjects. Sixteen (16) out of the twenty eight (28) patients were clear responders to rTMS. Two enrollees dropped out because of pain during stimulation, and three had possible adverse effects during the course of treatment that we were unable to connect causally with rTMS. Thus, it was found that rTMS could be used as a simple and effective treatment for many patients with refractory depression who would otherwise be candidates for ECT.

BRIEF DESCRIPTION OF THE DRAWINGS

FIG. 1 is a top view of a transcranial magnetic brain stimulator in accordance with the present invention while

DETAILED DESCRIPTION OF THE INVENTION AND THE PREFERRED EMBODIMENTS

The Magnetic Brain Stimulator

To accomplish the magnetic stimulation described in the present application, an improved apparatus for transcranial magnetic brain stimulation is disclosed herein, as further set forth below and in the accompanying drawings. The design of the apparatus is related to the designs previously described in U.S. Pat. No. 5,725,471, filed Nov. 28, 1994 and issued Mar. 10, 1998, the disclosure of which is fully incorporated herein by reference, and upon which the present application claims priority. Diagrams of the novel magnetic stimulator are provided in FIGS. 1–3. The specifications and details of the components of the stimulator are shown therein. The devices of the present invention induce electric fields similar in distribution to those from a Cadwell water-cooled figure-eight coil. However, the present inventions are much smaller, quieter, and more efficient, requiring no special cooling.

Figure 1:
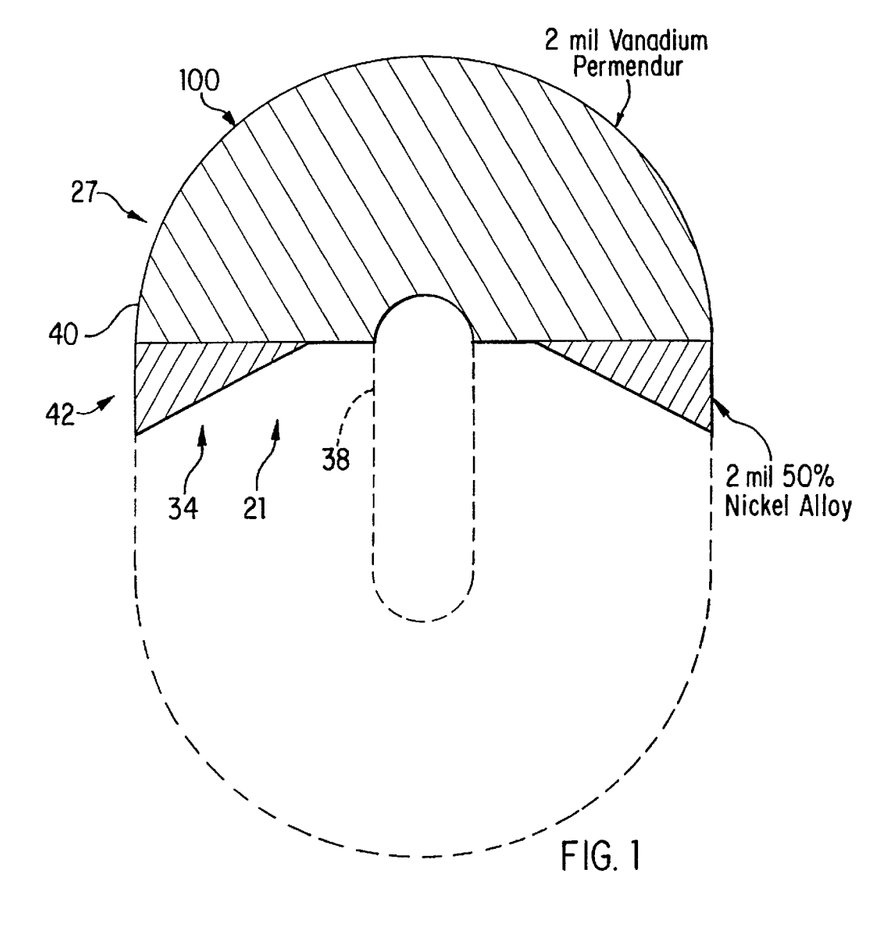
Figure 2:
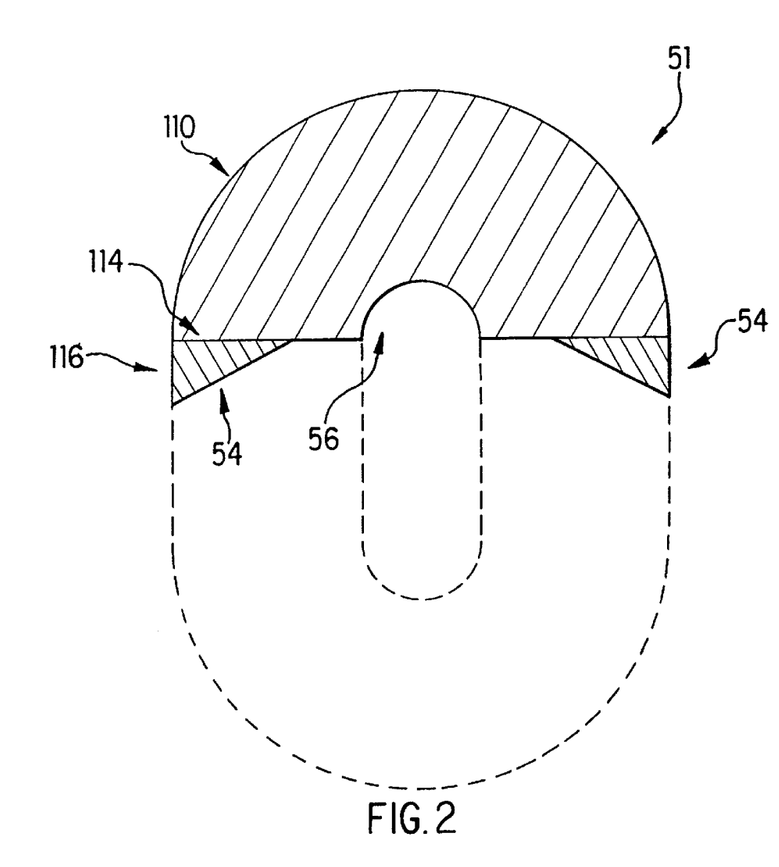
FIG. 2 is a top view of a second embodiment of a transcranial magnetic brain stimulator in accordance with the present invention with FIG. 2A being a side view thereof.

As shown in FIGS. 1 and 2, a core for a magnetic nerve stimulator is provided for stimulation of the brain. The stimulator core 27 is made of a magnetic material, preferably a ferromagnetic material. In the preferred embodiments, the material of the core has a magnetic saturability of at least 0.5 Tesla. Higher saturabilities are preferred, however, with saturabilities of at least 1.5 Tesla or higher, or even 2.0 Tesla or higher recommended in the preferred embodiments. Preferred materials for the core include vanadium permendur or 3% grain oriented steel.

As shown in FIG. 1, in the preferred embodiment, core 27 is cut from an oval winding of 2 mil vanadium permendur. Two cores can, in fact, be cut from a single oval winding, by cutting one core from each side of the oval. For illustration purposes, only a single core is shown in the diagram of FIG. 1.

The method of construction of such a core is as described previously in our patent, which is the parent to the present application, U.S. Pat. No. 5,725,471, issued Mar. 10, 1998. The best cores are constructed from thin laminate, highly saturable material (i.e. materials with a saturability of at least 1.5–2.0 Tesla, although less saturable materials with a saturability of 0.5 Tesla and higher can be used as well).

Figure 8:
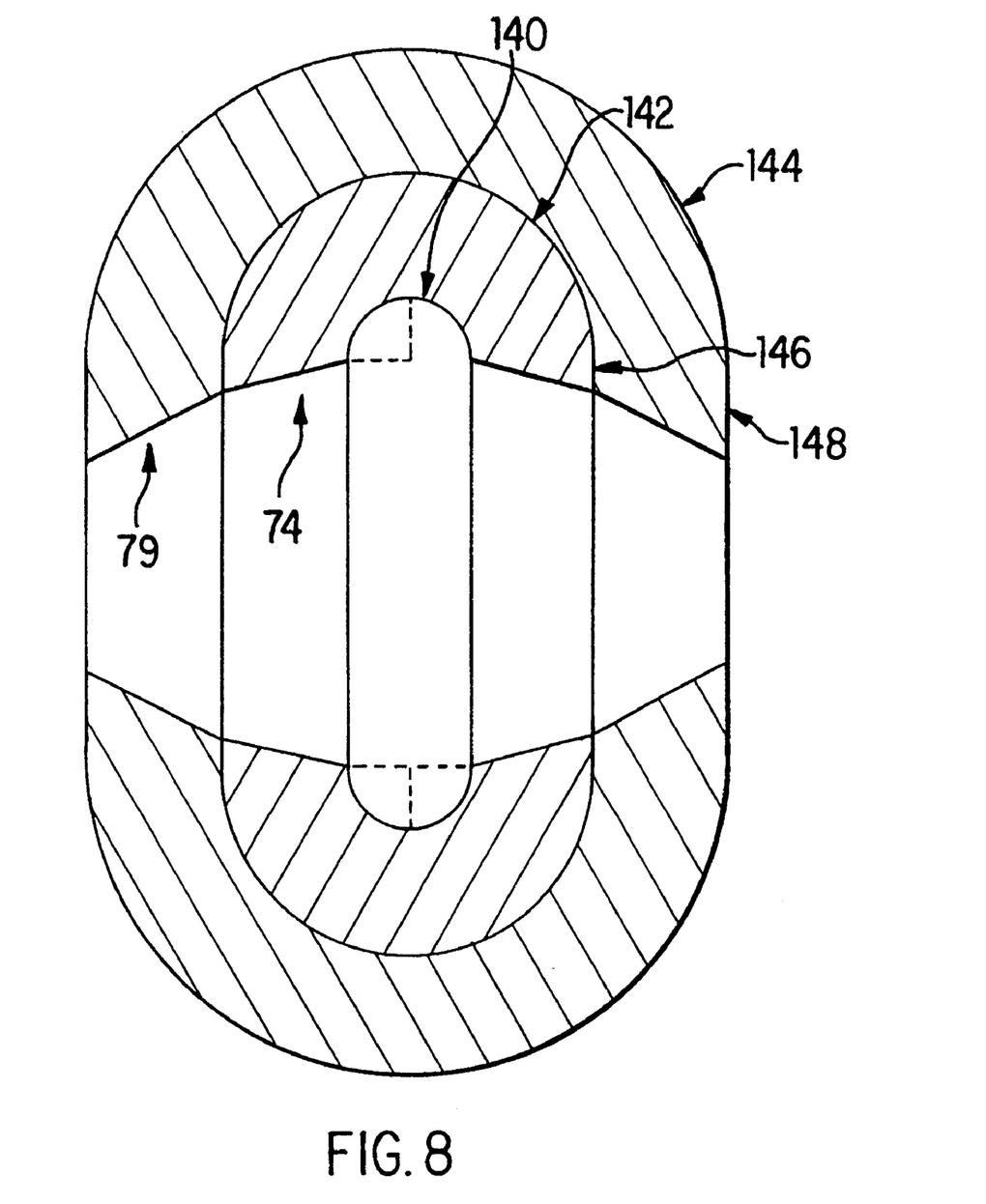
FIG. 8 shows the components used to form a third embodiment of a transcranial magnetic brain stimulator in accordance with the present invention.

A typical core can be wound using two mil stock of vanadium permendur. A long ribbon of such material is wound on a mandrel (e.g. a mandrel of wood or plastic) for the radius, thickness and depth desired. Each side of the ribbon is coated with a thin insulative coating to electrically isolate it from its neighbor. After cutting the core from the entire oval winding, a suitable core might span an angle of approximately 208°, or in the range of about 205–215°, as shown in FIGS. 1, 2 and 8. Other angles are possible, as well, however, though not preferred, as described below.

Once the ribbon has been wound on the mandrel to the desired dimensions, it is dipped in epoxy to freeze its position. Once the epoxy has dried, the mandrel is removed and the core may be cut for the span of angle desired. The cut may destroy the electrical isolation of adjacent laminations. Each cut must be finely ground so that it is smooth, and then a deep etch performed. The deep etch is performed by dipping each of the cut ends in an acid bath. This causes the cut ends to delaminate slightly, but maintains the electrical isolation of the laminations. Failure to perform this deep etch seems to result in considerable eddy current loss and heating at the cut ends of the core. Following the deep etch, the ends are brushed with epoxy to maintain the shape and structural integrity of the core. The final step of the construction is to wind a coil of insulated wire about the core. A typical inductance for a core of this type is about 20 $\mu$H. The present invention, however, may be practiced at other inductances or magnetic field strengths, if desired.

As an alternative to cutting the core as one entire section, the core can be cut as a semi-circular section. In this method of manufacture, the small triangular sections 34 at the bottom of the core are then cut separately, and attached to the semicircular section as shown in the Figures. Preferably, the smaller triangles are also made from vanadium permendur. If necessary, however, the triangles can be any material or alloy that has a saturation of at least 0.5 Tesla, and which can be worked by one of ordinary skill in the art. A suitable alloy for the triangular sections, for example, is 2 mil 50% nickel alloy.

Figure 1A:
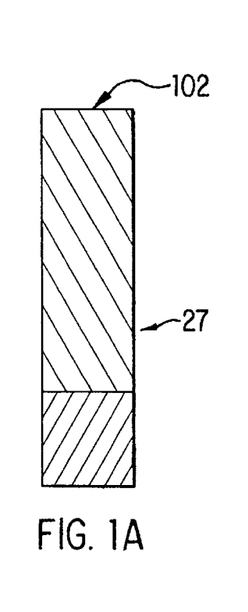
FIG. 1A is a side view thereof.

As shown in FIG. 1, in the preferred embodiment, core 27 has an outer diameter of approximately 4.75 inches. The core 27 has an inner semi-circular aperture 38 at the center of the core 27. Inner semicircle 38 has a diameter of approximately 0.75 inches. In a version where the smaller triangles are separate, triangular sections or wedges 34 are attached to the larger semi-circular section. Triangular sections 34 have a length on longer side 40, in contact with semi-circular section 30, of approximately 1.375 inches, and a length of approximately 0.75 inches on shorter side 42 which is approximately coplanar with the outside of semi-circular section 30. As shown in FIG. 1A, the cross sectional width of core 27 is approximately 0.625 inches.

Figure 2A:
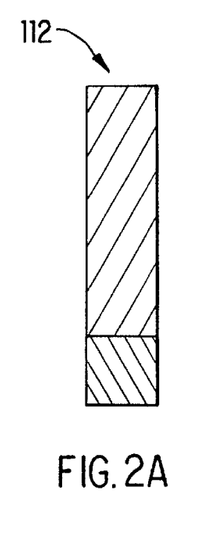

A second version of the core is shown in FIG. 2. Core 51 is merely a smaller version of the core 27 shown in FIG. 1. Core 51 has a outer diameter of 3.75 inches, and an inner diameter 56 of approximately 0.875 inches. The triangular sections 54 attached to the ends of the semi-circular core have a length of approximately 0.47 inches on shorter side 116 and a length of approximately 0.875 inches on longer side 114. As mentioned with respect to FIG. 1, the cores are preferably cut such that the triangular sections 54 are an integral part of the core 51, however, the triangular sections 54 can be cut separately and attached to a semi-circular section of core, if necessary or desired. In the preferred embodiment, the core with triangular sections subtends an angle of approximately 208 or 205–215 degrees as measured from the center of inner diameter 56 to the far edge of shorter side 116. This embodiment shows the core as having a thickness of about 0.5" (FIG. 2A).

A third embodiment of the core is shown in FIG. 8. In this embodiment, two separate layers of materials are used. An inner layer 74 is provided which is constructed of 2 mil vanadium permendur. Outer layer 79 is constructed of 2 mil 50% nickel alloy. The preferred dimensions of the respective layers are as follows: inner diameter 140 of inner layer 74 is preferably 0.875 inches, and outer diameter 142 of inner layer 74 is preferably 2.625 inches. The inner diameter of outer layer 79 is the same as the outer diameter of inner layer 74. Outer diameter 144 of outer layer 79 is preferably 4.375 inches. The horizontal dotted line indicates where the semi-circular portion of the winding ends and the triangular pieces begin. The short side of inner triangle 146 is preferably 0.21875 inches, and the short side of outer triangle 148 is preferably 0.6875 inches. The overall thickness of the embodiment is preferably 0.625 inches. The inner and outer ovals are wound and separately cut. A single oval can be used to cut two inner cores, and a second oval can be used to cut two outer cores. The inner layer 74 and the outer layer 79 are then nested together as shown in FIG. 8.

As shown in the Figures, each of the cores of the stimulator is preferably an open core, i.e. the core forms an open arc, and does not constitute a closed toroid. An approximately C-shaped core is preferable. In accordance with the present design, at least a portion of the core of the stimulator conforms, at least approximately, to the shape of the head. In the preferred embodiment, a hemispherical stimulator, having at least one, but preferably four adjacent, cores (see FIG. 3) made of saturable or highly saturable ferromagnetic material, is used, as shown in the Figures.

The span of the core affects both the penetration depth of the magnetic field and the magnitude of the field. While a variety of angles are acceptable for the curvature of the arc of the core, a core of 208 degrees or approximately in the range of about 205–215 degrees is shown in the Figures for preferred embodiments. In other embodiments, cores of approximately 190–230 degrees can be utilized. Alternatively, a core spanning an arc of approximately 180–270 degrees is also possible, although not necessarily as effective.

Figure 3:
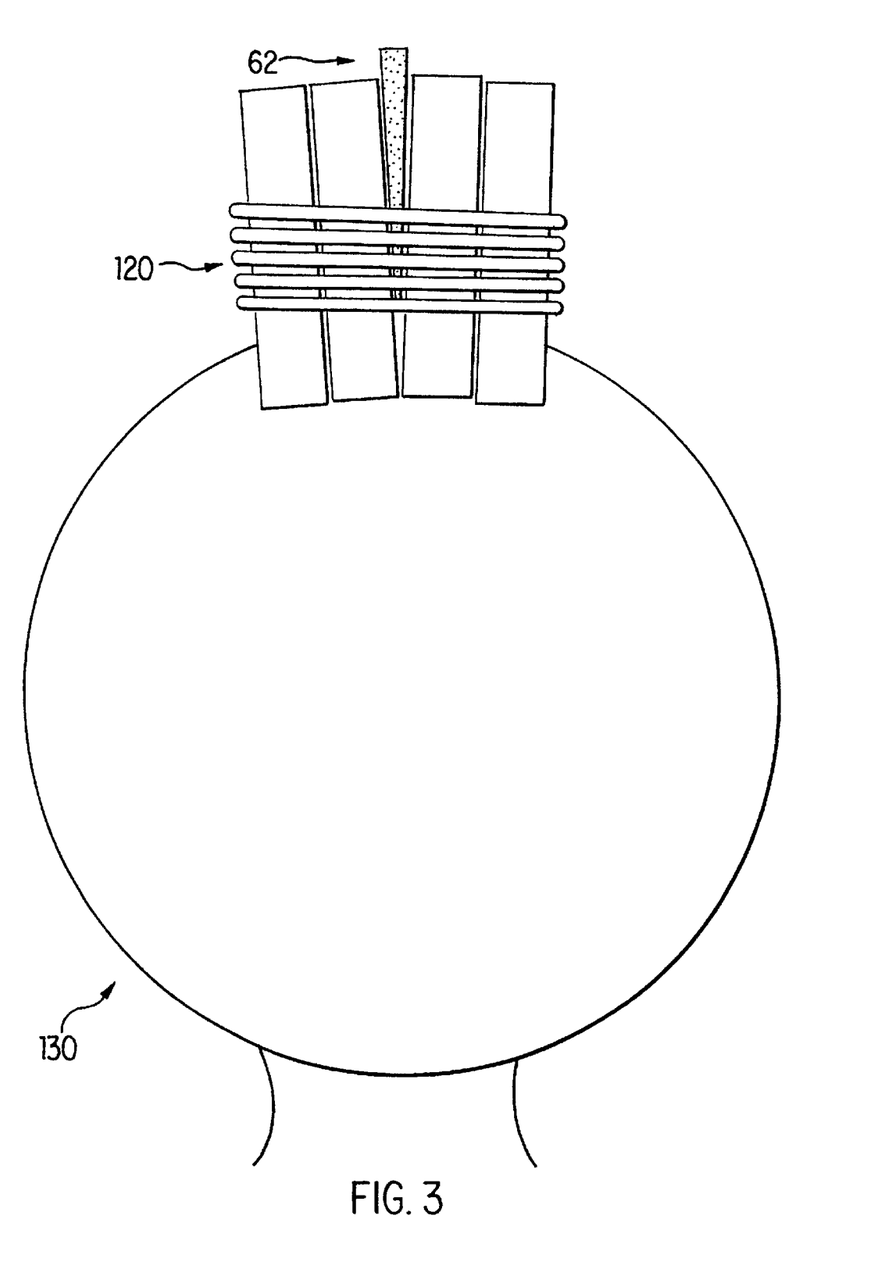
FIG. 3 is a front view of a transcranial magnetic brain stimulator formed from 4 cores in accordance with FIGS. 1 or 2, as positioned on a schematic human head.
Figure 4:
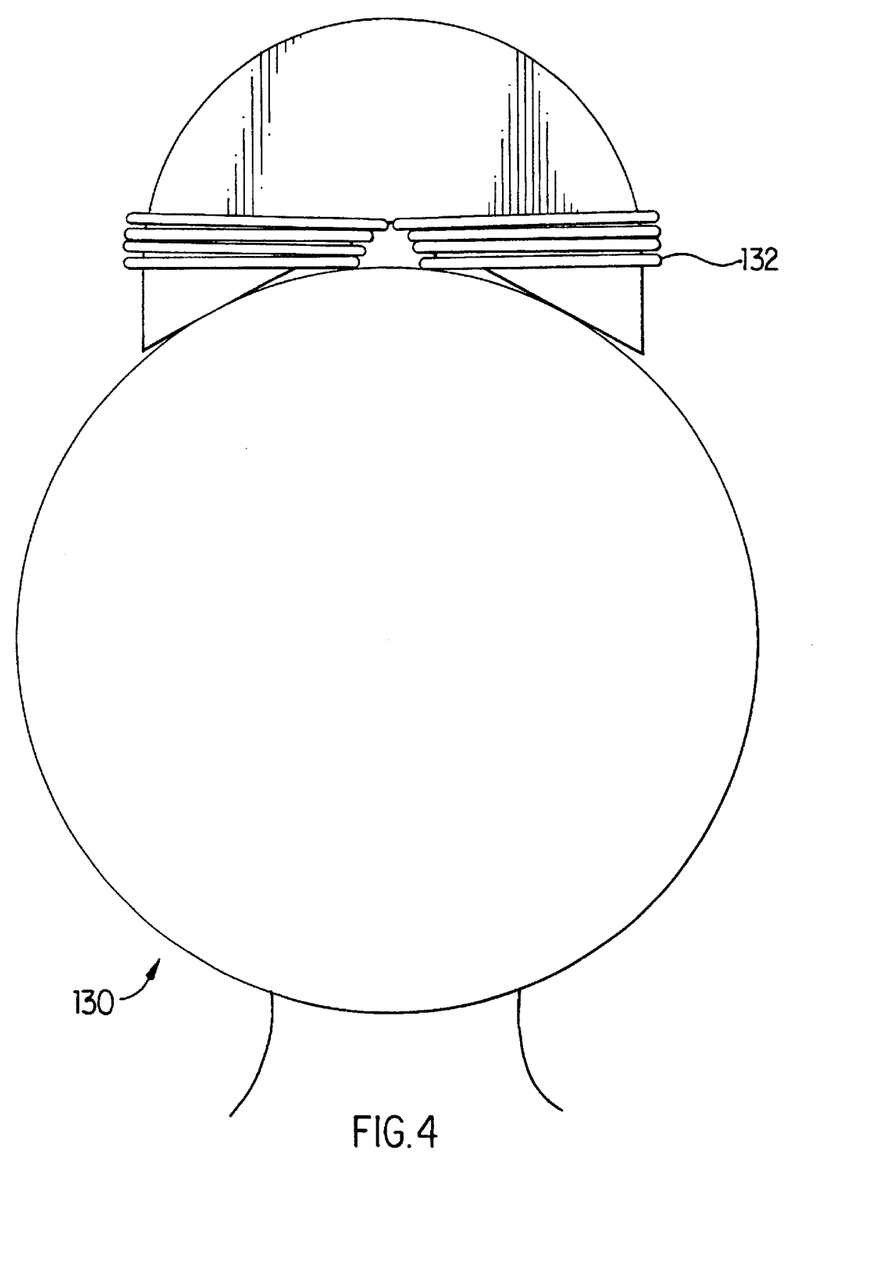
FIG. 4 is a side view of the stimulator of FIG. 3 on a schematic human head.

In the preferred embodiment, to form the stimulator, four cores are positioned approximately side by side to form a complete magnetic stimulator. Although more than four cores or less than four cores are possible, four are preferred. As shown in FIGS. 3 and 4, two pairs of cores are placed side by side to form a hemisphere designed for placement on the head. The combined cores are wound with a series of windings of wire. In the preferred embodiment, approximately nine to ten turns of wire are used; approximately nine (9) turns of wire being preferably wound around the larger stimulator formed of cores of FIG. 1, and approximately ten (10) turns of wire being wound around the smaller stimulator formed of cores of FIG. 2. As shown in FIGS. 3 and 4, approximately four–five (4–5) turns of wires are wound around each half of the stimulator, i.e., approximately four to five turns are wound around a first side of the stimulator, and another four to five turns are wound around the second side of the stimulator.

In accordance with the present invention, it is also preferred that the stimulator be provided with a visualization and location port for viewing and marking the head and locating the stimulator thereon. In the present invention, a space is left open between the two pairs of cores to form a center port 62 (see FIG. 3). Center port 62 extends from the top of the stimulator down to the surface of the patient's head as shown in FIG. 3. It is preferred that a length of plastic or copper tubing be inserted in this area to form the port. Port 62 is of sufficiently large diameter that a marking device such as a pen or felt marker can be inserted into the port 62 through the stimulator to mark the head's surface (or to mark a cap worn on the head). Thus, as an illustration of the construction of the port 62, the internal ink containing cylinder can be removed from a standard writing device, such as a Papermate™ pen, leaving the pen's outer plastic section of tubing empty. This outer plastic section of tubing can be inserted between the two pairs of cores to serve as the tubing for the port. The internal, ink containing portion of the pen can later be inserted down and through this port to mark the patient's head. Any suitable tubing and any marker of smaller diameter than the tubing, can, of course, be used, and the present example is not meant as a limitation.

Port 62 has importance both as a means to precisely mark where a stimulator is located on the head, and as a means to precisely position the stimulator. When the stimulator is placed on the head, the marking device or pen can be inserted down the port and through the stimulator to make a mark on the head of the patient. The mark serves as an effective reference, indicating exactly where the stimulator was positioned. This provides a convenient and effective means of precisely recording the stimulator location for later reference.

Likewise, if it is desired that the stimulator be centered over a particular region of the head a mark can first be placed on the head in the appropriate area. Or, if it is desired that the stimulator be placed on the same location in successive sessions, an appropriate mark can be left on the head after the first positioning. In either situation, by viewing or inserting a probe down the port of the stimulator, the stimulator can be moved around over the head until the marked area is identified through the port, so that the stimulator can be positioned on the exact location desired.

Figure 7:
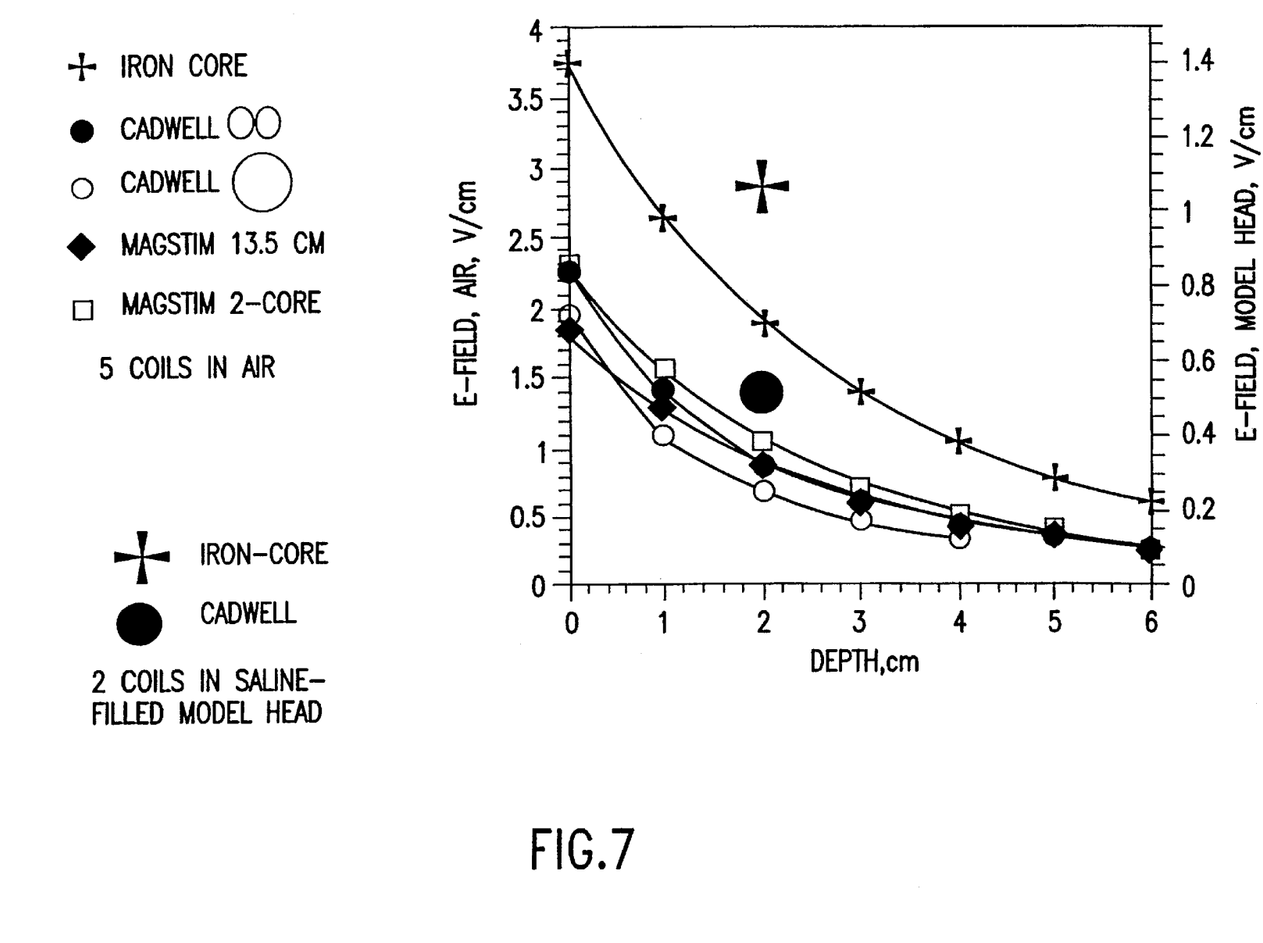
FIG. 7 is a graph showing comparative results for use of the present stimulator in comparison to several other devices.

FIG. 7 shows a comparison of several coils at 30% output, measured in air. At the critical depth of two cm below the coil, the present ferromagnetic core system, as disclosed herein, induces approximately twice the electric field of an oversized plain coil, and more than twice that of a standard commercial coil from Cadwell. The power improvement is the square of this ratio.

Thus, in the present design, the semi-circular configuration optimally combines with a double-loop wire coil, and the concave active surface delivers maximal magnetic flux to the brain and other physiological targets. Of the large number of other magnetic stimulators that have been developed or are in use, the present inventors are not aware of any other design having comparable advantages or performance. In the present device, focal magnetic stimulation is provided with an approximate twofold amp-turn efficiency and ¼th the heat generation of prior available stimulation coils without a ferromagnetic core. Triangular extensions and curvature of the active surface significantly improve efficiency of brain stimulation. The device allows more powerful and focused stimulation than any existing alternative, and, alternatively, allows conventional stimulation at a much lower energy cost. It uniquely allows continuous high speed magnetic stimulation without requiring special provisions for cooling. Moreover, projection of the magnetic field into the brain is effective even when the core is partially saturated.

In the preferred embodiment of the present invention, the electrical circuitry and parameter referred to in co-pending application Ser. No. 08/345,572 filed Nov. 28, 1994 are employed with the stimulator taught herein. Alternatively, any other suitable circuit and power source can be used as well be apparent to those of ordinary skills in the art.

Magnetic Brain Stimulation for Localization of Language Function

Among the many suitable applications of this device, the present inventions may be used to provide an improved technique for active localization and characterization of brain function. In one particular embodiment, it is possible to locate and characterize language function. This technique was tested on four subjects, all being right-handed male physicians, ages 31–49, studied under informed consent. All had previously shown dominance for magnetic speech arrest over the left hemisphere. (See, e.g., Epstein, 1996, cited below)

For magnetic mapping, the subjects were seated comfortably and unrestrained. The head was covered with a thin latex swim cap, which simplified position measurements over a large scalp area that included up to 100 possible sites of stimulation. Any redundant latex folds were taped down, and the position of the cap was labeled using as landmarks the inion, distance from nasion, earlobes, and vertex. One-centimeter grid lines were drawn over the posterior frontal region and labelled alpha-numerically. Relaxed motor threshold was determined as previously described, (See Epstein, 1996, cited below) using the dominant first dorsal interosseous (FDI) or abductor pollicis brevis (APB) to represent the hand. With this technique, threshold is defined as the lowest intensity of stimulation that produces compound motor action potentials (CMAPs) of 50 $\mu$V or greater on five of ten trials; (See, e.g. Pascual-Leone, 1993, cited below) consequently averaged CMAPs are expected to be non-zero at threshold.

Mapping of CMAPs from FDI or APE was performed using the disclosed ferromagnetic core (vanadium permendur) stimulation coil, with the induced electric field maximum beneath the center point of the device. A small port through the middle allows precise marking and positioning. The coil was placed so that the induced electric field was aligned horizontally—that is, along a sagittal or axial plane. With the right hand relaxed, we averaged eight responses to left hemisphere stimulation at a rate of 1 Hz. Testing was extended in all directions on the grid until a 2-cm rim of absent responses completely surrounded the area of activation. Mapping was done in the same manner from the right orbicularis oris (ORO) in all subjects, but facilitation was used if no response could be obtained during relaxation at stimulator outputs up to 20% greater than hand motor threshold.

Speech interruption was tested with the same coil while the subject counted briskly and repetitively upward from one to 20. The stimulator was activated at a rate of four Hertz about the time the count reached the number "five." Stimulator output was adjusted differently in the four subjects, from a level that barely produced complete speech arrest to intensities 5–10% higher. The degree of speech interruption was rated by both subject and observers as complete, moderate, slight, or absent.

In a separate session, the stimulation coil was repositioned over the area of maximum speech arrest. After obtaining appropriate baselines, the following tasks were carried out during stimulus trains of 3–5 seconds duration:
  reading unfamiliar material aloud;
  reading silently and then describing content;
  spontaneously describing the events of the "cookie theft picture";
  hearing and obeying two-step commands with inverted syntax;
  visual confrontation naming, using slide projections of 14 familiar objects;
  writing numbers from "one" upward;
  repetition of two brief phrases, including "no ifs, ands, or buts";
  singing lyrics to a familiar song;
  tests of oral praxis, including tapping the upper teeth with the tongue, licking the lips from side-to-side, and alternating lip puckering and blowing.

Writing and visual confrontation naming were then repeated with the stimulator placed 2 cm anterior to the position of maximum speech arrest. Singing was repeated during stimulation of the homologous area over the right hemisphere. A delay of ten seconds or more was always present between stimulus trains.

For construction of a two-dimensional map, the average CMAPs representing each muscle were scaled to a maximum of one. Complete speech arrest was arbitrarily assigned a magnitude of 1.0, moderate speech interruption 0.5, and slight speech interruption 0.25. Bubble charts were plotted with the area of each bubble corresponding to the magnitude of the response at that site. For each muscle and for speech arrest, a two dimensional mean position on the grid was calculated. These positions were marked on the swim cap, which was then replaced on the subject's head and realigned to the previous anatomic landmarks. Each center of gravity was marked with a capsule of vitamin E for identification on MRI. Cranial MRI was then performed.

Measurement of the induced electric field was performed in a spherical, saline filled model head of radius 7.5 cm, using a differential probe with silver-silver chloride electrodes as previously described. (See Epstein, 1996, cited below). This was followed by three dimensional reconstruction of the MRIs.

In this test of the invention, complete speech arrest was obtained over the left posterior-lateral frontal lobe during counting and reading aloud in all four subjects. In three subjects counting and reading were entirely normal on right-sided stimulation at the same intensity. The other subject had slight dysarthria with stimulation on the right. Remarkably, visual confrontation naming was intact for most objects in all subjects, with variable slowing of responses and slight dysarthria. Rare aphasic errors usually consisted of word substitutions. Writing numerals was intact in the right hand at both left frontal sites of simulation, even though one subject had slight jerking of the right upper extremity. The other three subjects underwent a second writing test in which they spelled out the numbers, again with no difficulty. Singing was consistently easier than spontaneous speech, with slight to moderate slowing or dysarthria but with preservation of melody. However, in two of three subjects so tested, stimulation over the right hemisphere produced flattening and loss of melody that was apparent to both the subject and the observers, This effect was obtained in one subject as the same intensity used for speech arrest, and in the other only at a setting 10% higher.

Resting motor maps were easily constructed for the hand using FDI in three subjects and APB in one. Only two subjects had facial CMAPs obtainable from the ORO at rest. The other two maps of ORO were obtained with facilitation: one subject gently pursed his lips, while the other counted aloud during averaging of CMAPs.

In one series of tests, speech arrest was tested at a relatively low intensity, equal to 95% of resting threshold in FDI. In another series of tests, speech was tested at a higher relative intensity of 118%, and facilitation was not necessary for recording of facial CMAPs. But the use of different hand muscles and different kinds of facilitation for ORO had little effect on the relative map positions. The area of stimulation that produced speech arrest was always congruous with the area which gave motor responses from ORO. In the coronal plane, the center of gravity for SA lay an average of 0.5 cm from that for ORO. In the axial plane, the center of gravity for SA lay, on average, 0.7 cm posterior to that for ORO.

The smallest rectangle of the mapping grid that encloses the sites of speech arrest can be described as the "local area." Within the local area, the first two subjects showed no correlation between the degree of speech arrest and the magnitude of facial muscle contraction. A significant correlation was found for subjects 3 and 4, in the latter the level of stimulation was relatively high during language mapping. Thus, the congruence for speech arrest and facial movement was not consistently present on a detailed level.

Through our studies it has therefore been found that magnetic stimulation of the dominant hemisphere produces specific impairments of language output, and not simply anarthria: some modalities of speech are affected profoundly, but others minimally or not at all. Magnetic interference most affects spontaneous speech. It has less effect on repetition, confrontation naming, and singing, while writing is entirely spared. Magnetic speech arrest is not Broca's aphasia. The site of action is congruous with the region of facial motor responses, rather than anterior to the motor strip as might be expected from classic models of language organization.

During neurosurgical mapping procedures, with direct electrical stimulation of the cortex, speech arrest can be obtained over extensive areas of both hemispheres. The most frequent site is the facial portion of the primary motor area, near the junction of the Sylvian and Rolandic fissures. (See, e.g. Penfield, 1950 and Ojemann, cited below) This is the same region implicated in magnetic speech arrest over the dominant hemisphere. In contrast with electrocorticography, however, magnetic stimulation produces speech arrest in only one location, and has little effect on confrontation naming in this area or anterior to it.

Many features of magnetic speech arrest are similar to those of the articulatory disorders variously described as pure motor aphasia, pure anarthria, cortical dysarthria, simple aphasia, phonetic disintegration, and aphemia. Such cases have been described with subcortical lesions of the lateral frontal region, but when cortical lesions are responsible they are found in the lower motor strip and Rolandic operculum. Clinical findings include marked slowing of speech output, stuttering, preservation of grammar, and relative preservation of repetition and singing. Writing is generally spared. Many authors, including Pierre Marie, distinguish a pure articulatory disturbance from aphasia on the bases of intact comprehension, reading, and writing. (See, e.g. Marie and Schiff, cited below) Others have noted the frequent association with lexical errors (Kaminski) and other forms of language disorganization, and prefer to classify aphemia as a limited form of aphasia (L&L).

The function most impaired by magnetic stimulation is the de novo assembly of spontaneous speech and the complete arrest of language output by stimulation races as low as two per second is a striking feature. The rapid, precise, coordinated synthesis of multiple lingual-buccal-vocal movements into consecutive phonemes represents one of the most extraordinary tasks carried out by the human motor system, and it's reasonable to hypothesize that a specialized language module may be dedicated to it. Such a module would be tightly interwoven with the primary motor cortex; as a final common pathway it might be more difficult to bypass with parallel pathways of language processing. Magnetic interference with speech may be lessened when the construction of phonemes is cued by speech reception, melody, or the presentation of familiar visual objects. This amelioration of the deficit by other neural inputs stands in distinction to aphemia and also to the classical aphasias, all of which are characterized by impairment of repetition.

Functional maps of the type used here have important limitations, including the relatively large area and elliptical shape of the induced electric field. This shape produces a well-known distortion of the magnetic map, in which sites of excitation are "smeared" more extensively in the direction of the electric field. Assuming that spatial smearing is symmetrical, however, the scalp center of gravity as calculated here will be unaffected, and should accurately reflect the mean position of excitation even in the absence of formal deconvolution.

In comparison to electrocorticography, magnetic mapping of the cerebral cortex has important advantages that go beyond its relative safety and ease of uses. One of these, obviously, is the ability to study both hemispheres of the normal brain. Another is the robustness of motor effects. Direct electrical stimulation of the cortex in conscious subjects fails to activate any hand movement in as many as 35%, fails to produce movement of the face or tongue in up to 83%, and occasionally fails to identify areas of speech arrest anywhere in the dominant hemisphere. Thus it is often impossible, using electrocorticography, to make a clear physiological distinction between different cortical regions; there simply are not enough sites of activation in a given subject. But with appropriate techniques magnetic stimulation will always activate movement of multiple hand muscles in normal subjects, and has produced speech arrest in all but one of several dozen normal subjects we have surveyed thus far. The reason for this surprising advantage of transcranial magnetic stimulation is unknown, but may relate to a consistent electric field vector over a larger volume of cortex.

Our technique has not yet been validated against the Wada test, and thus cannot necessarily substitute for it at present. However, the usual Wada test patient who harbors intractable epilepsy and a high incidence of structural lesions may have atypical patterns of language organization. The Wada procedure is also complicated by a limited time frame and unpredictable drug effects, so that its results may not extrapolate to the normal population.

Analysis of magnetic speech arrest supports the current interpretation of language organization as modular, rather than the older concept of a single output area that controls multiple functions. The robustness and convenience of magnetic mapping should further facilitate the investigation of language function in normal brains, and improve our understanding of recovery in those that have suffered impairment.

Magnetic Brain Stimulation for Treatment of Depression

In accordance with the present invention, the present apparatus can also be used for the treatment of depression. It has been found that magnetic transcranial brain stimulation can be an effective treatment in a variety of patients, including those who are psychotically depressed or medication resistant. Treatment of refractory depression using the present device having a core of a magnetic or preferably ferromagnetic material is believed to be more effective than use of the devices previously disclosed in the art. Although the use of left prefrontal rTMS is preferred based on current understanding, it may be possible that other forms of stimulation will be found useful with further studies.

In accordance with the present invention, the location of the right hand motor area and relaxed motor threshold are first identified over the left hemisphere. (See e.g., Epstein C M, Lah J K, Meador K, Weissman J D, Gaitan L E, Dihenia B, Optimized stimulus parameters for lateralized suppression of speech with magnetic brain stimulation, *Neurology*, 1996; 47: 1590–1593, the disclosure of which is fully incorporated herein by reference). During stimulation at a rate of 1 Hz, the magnetic coil is moved across the left central region and the stimulator output is gradually adjusted to locate the point of lowest-intensity activation, followed by the magnetic threshold at that site. This position is then labelled with a permanent marker. Determining motor threshold requires only approximately 5–10 minutes at the first treatment session, and less time in subsequent sessions because the location has already been marked. Location of the marked area is facilitated by the use of center port 62.

The site of rTMS treatment is measured 5 cm anteriorly from the hand motor area on a parasagittal line. (See e.g., George M S, Wasserman E M, Williams W., et al., Changes in mood and hormone levels after rapid-rate transcranial magnetic stimulation of the prefrontal cortex, *J. Neuropsychiatry Clin. Neurosci.* 1996; 8:172–180, the disclosure of which is fully incorporated herein by reference.) At each rTMS treatment, the stimulator output is set to 110% of relaxed motor threshold and a repetition rate of 10 Hz. Stimulation is delivered in ten trains of 5 seconds each, with trains beginning 30 seconds apart. The coil is oriented so that electric fields are induced along a sagittal plane. Ear protection was worn throughout.

During use of the device for treatment, all treatments were administered once daily for five (5) consecutive weekdays. Patients lay supine with the head elevated on a pillow. Continuous cardiac monitoring was performed, and blood pressure was taken every 60 seconds during stimulation. rTMS was performed using a damped cosine pulse and the ferromagnetic core stimulator disclosed herein.

Figure 5:
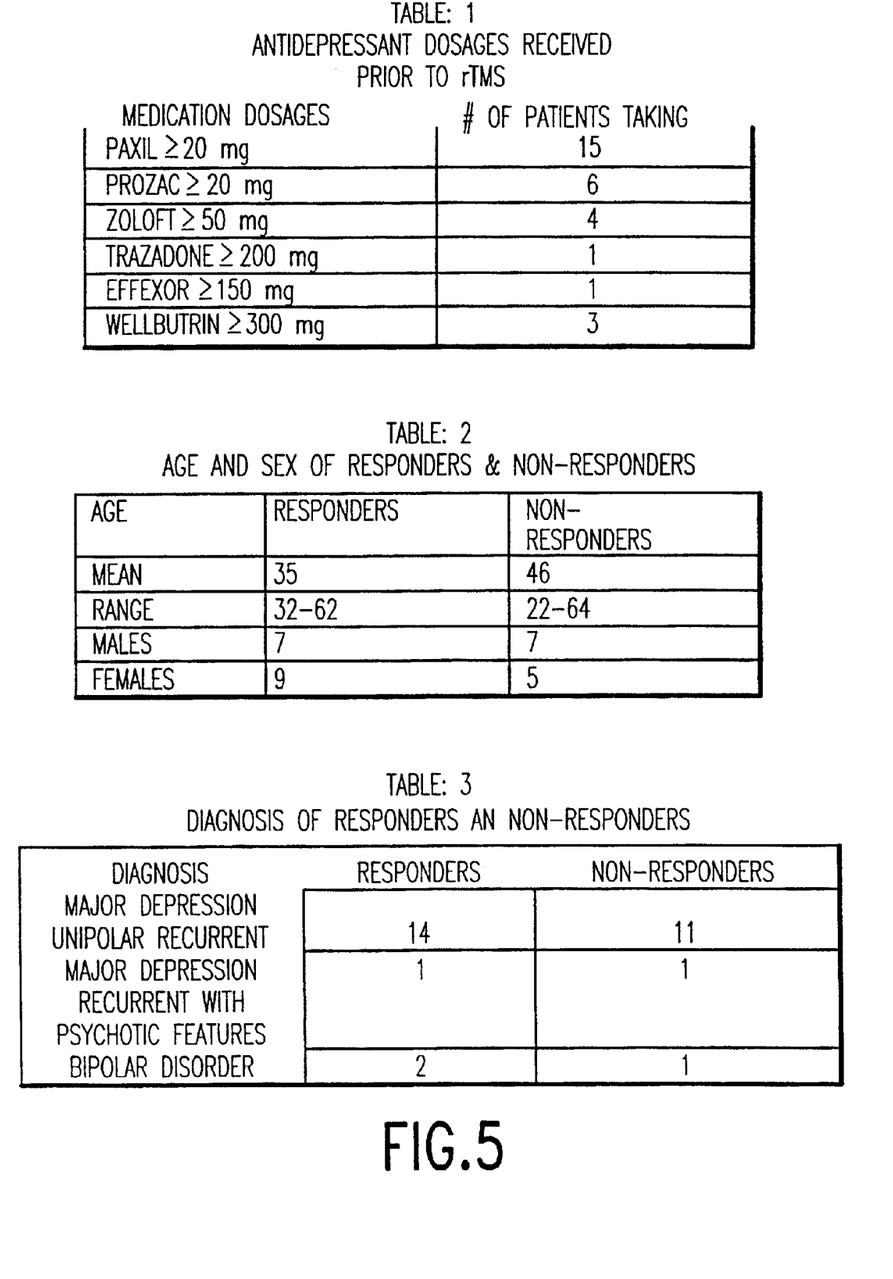
FIG. 5 presents a series of three tables showing experimental results from the use of the present stimulators for the treatment of depression. Table 1 shows the antidepressant dosages of indicated medication received by experimental subjects prior to rTMS. Table 2 shows the ages and sex of the responders and non-responders to treatment. Table 3 shows the diagnoses of the responders and non-responders to treatment.

Using this magnetic stimulator, left prefrontal rTMS was effected with good results. The device and method were tested on 32 patients who had been referred for electroconvulsive therapy (ECT). Ten patients had previously received ECT. All patients studied had received at least one six week trial of an antidepressant at a therapeutic dose (See Table 1 of FIG. 5). All of the patients met DSM-IV criteria for a Major Depressive episode (29 unipolar, 3 bipolar), were rated at least moderately ill on the Clinical Global Impression Scale (CGI) and had a pre-treatment score on the Hamilton Depression Scale (Ham-D, 21 item) greater than 20. Diagnoses were made by a physician (GSF) using a DSM-IV checklist during a structured clinical interview.

In general, patients were tapered off psychotropic medications prior to beginning a course of rTMS, although in our studies, four of the patients could not be taken off of medications due to the severity of their illness. In no case was a patient started on a new psychotropic medication during rTMS treatment. Patients with a history of recent myocardial infarction, cardiac pacemaker, intracranial metallic objects or increased intracranial pressure were excluded. Responders were characterized according to the criteria of Sackheim, et al.: they had to show a 60% reduction from their pre-treatment Ham-D score and a post-rTMS maximum score of 16 points. (See, Sackheim H A, Decina P, Portnoy S, Kanzler M, Kerr B, Malitz S., Effects of electrode placement on the efficacy of titrated low-dosage ECT, *Am. J. Psychaitry*, 1987; 144: 1449–1455, the disclosure of which is fully incorporated herein by reference.) In addition, responders had to be rated as moderately to markedly improved on a 7 point CGI. These ratings were completed by the patient's clinical treatment team along with the physician on the rTMS service (GSF). All ratings were obtained prior to beginning rTMS and within 48 hours after the fifth treatment.

Figure 6:
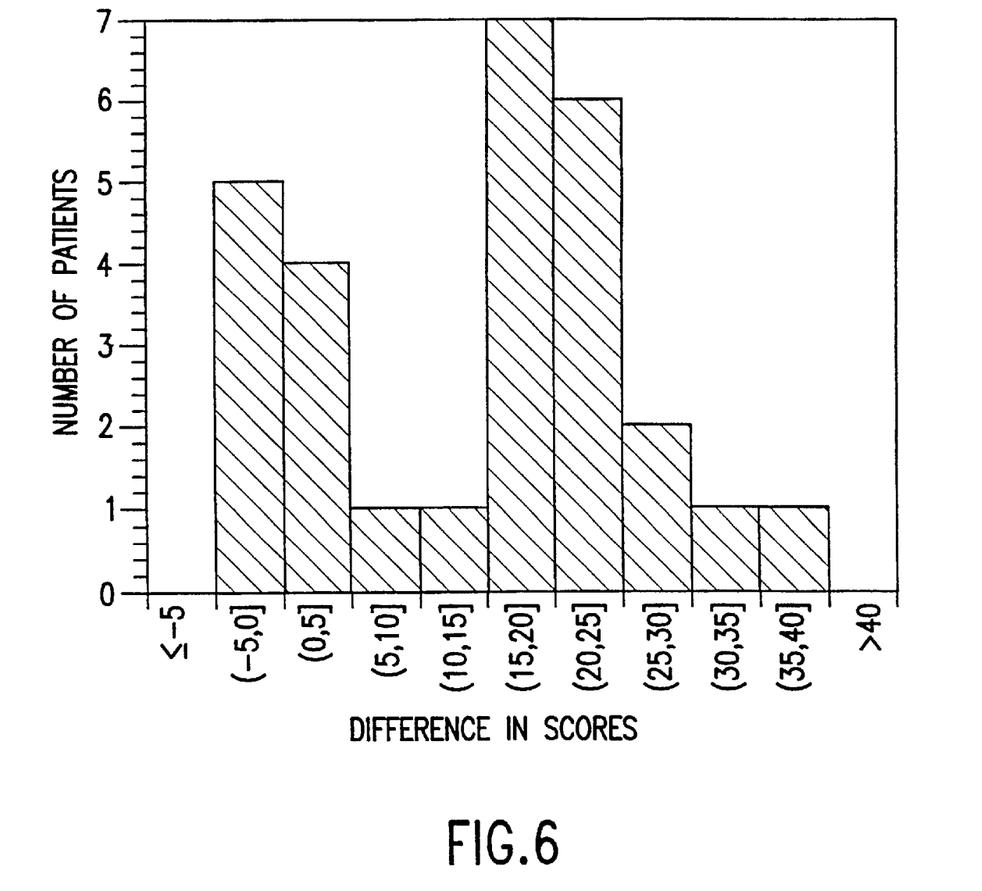
FIG. 6 is a histogram of the differences between post-treatment and pre-treatment Hamilton Depression scores for all patients completing a course of rTMS.

Of those patients studied, 28 out of 32 completed the course of rTMS treatments. Mean Ham-D scores fell from 31 to 15 (p<0.0001). There were 16 responders (56%) and 12 non-responders (44%). Fourteen patients (50%) had post-treatment Ham-D scores of less than 10. When the differences in post-treatment and pre-treatment Ham-D scores were plotted on a histogram, the non-responders and responders appeared to fall into two distinct clusters (See FIG. 6). Patients who responded to rTMS did not differ with respect to age (p=0.3), sex (p=0.5) or pre-rTMS Ham-D scores (p=0.4) from non-responders (See Table 2 in FIG. 5). Fourteen of the 25 (56%) patients with Major Depression (Unipolar, Recurrent) responded to treatment using the present stimulator. One of the 2 patients with Psychotic Depression responded (See Table 3 in FIG. 5). Two of 3 patients with Bipolar Disorder responded to rTMS using the present stimulator (See Table 3 in FIG. 5). Of ten patients who reported a favorable response to ECT in the past, 8 of these responded to rTMS using the present magnetic stimulator.

Accordingly, the present device and method has been found to be useful for treatment of depression as an alternative to the devices and methods previously used in the art.

In several patients studied, however, some adverse events were reported. Two patients (a 47 year old male and a 33 year female) requested termination after one treatment because of pain over the left frontal region during stimulation. In both cases, the pain stopped immediately, when stimulation ceased.

A 44 year old female with preexisting motor tics of the right and lower extremity had recurrence of these movements during the first rTMS treatment. Periodic limb flexion persisted for 20 minutes without change in speech or alertness, and could be quenched repeatedly with gentle pressure to the arm or leg. Movements ceased after 2 mg of lorazepam IV, without any subsequent complications.

A 51 year old hypertensive female developed left arm, leg, and lower face paresthesias 20 minutes after her first rTMS treatment. Paresthesias remitted completely over several days. Complete neurological examination five hours after onset was normal. MRI and MRA the next day were normal. This event was assessed as a probable small lacunar infarction in the right hemisphere.

A 46 year old female, who was a responder to rTMS, initially reported that she had no history of epilepsy prior to beginning treatment; however, two weeks after starting treatment she reported apparent left focal motor seizures, and admitted preexisting twitching of the left face. All episodes were remote from the times of rTMS by at least several hours. Complete neurological examination, EEG, and MRI were normal. Seizures continued and became bilateral despite therapeutic phenytoin levels, and were highly correlated with attendance at church and funerals. She underwent inpatient video-EEG monitoring, which confirmed a diagnosis of psychogenic pseudoseizures.

Ten patients complained of mild headache during treatment. These headaches ended immediately after stimulation stopped; all ten patients completed the course of rTMS, and none required treatment with analgesics. No patients complained of memory or cognitive side effects during or after rTMS. rTMS had no effect on blood pressure or heart rate.

Accordingly, the present inventions are believed to be significant improvements over the prior art, and have application in characterization, localization and treatment of brain function, including for depression and speech arrest. In addition to the disclosure of the inventions provided herein, several additional references may be of interest to those of ordinary skill and useful for additional background and information of relevance. These references include:

1. Pascual-Leone A, Gates J R, Dhuna A. Induction of speech arrest and counting errors with rapid-rate transcranial magnetic stimulation. Neurology 1991;41:697–702.
2. Michelucci R, Valzania F, Passarelli D, et al. Rapid-rate transcranial magnetic stimulation and hemispheric language dominance: usefulness and safety in epilepsy. Neurology 1994;44:1697–1700.
3. Jenum P, Friberg L, Fuglsang-Frederiksen A, Dam M. Speech localization using repetitive transcranial magnetic stimulation. Neurology 1994;44:269–273.
4. Pascual-Leone A, Houser C M, Reese K, et al. Safety of rapid-rate transcranial magnetic stimulation in normal volunteers. Electroenceph Clin Neurophysiol 1993;89:120–130.
5. Lesser R P, Luders H, Klem G, et al. Extraoperative cortical functional localization in patients with epilepsy. J Clin Neurophysiol 1987;4:27–53.
6. Ojemann G A, Sutherling W A, Lesser R P, Dinner D S, Jayakar P, Saint Hilaire J-M. Cortical stimulation. In: Engel J, Jr, ed. Surgical treatment of the epilepsies. 2nd ed. New York: Raven Press, 1993:399–414.
7. Cherlow D G, Dymond A M, Crandall P H, Walter R D, Serafetinides E A. Evoked response and after-discharge thresholds to electrical stimulation in temporal lobe epileptics. Arch Neurol 1977;34:527–531.
8. Epstein C M, Schwartzberg D G, Davey K R, Sudderth D B. Localizing the site of magnetic brain stimulation in humans. Neurology 1990;40:666–670.
9. Wassermann E M, McShane L M, Hallett M, Cohen L G. Noninvasive mapping of muscle representations in human motor cortex. Electroenceph Clin Neurophysiol 1992;85:1–8.
10. Sackeim H A, Decina P. Portnoy S. Kanzier M. Kerr B. Malitz S. Effects of electrode placement on the efficacy of titrated low-dosage ECT. Am J Psychiatry, 1987; 144:1449–1455
11. Pascual-Leone A, Houser C M, Reeves K, et al. Safety of rapid-rate transcranial magnetic stimulation in normal volunteers. Electroencephalogr Clin Europhysiol. 1993; 89:120–130.
12. Wasserman E M, Grafinan J, Berry C, Hollnagel C, Wild K, Clark K, Hallett M. Use and safety of a new repetitive transcranial magnetic stimulator.
13. Hufnagel A, Claus D, Brunhoelzl C, Sudhop T. Short-term memory: no evidence of effect of rapid-repetitive transcranial magnetic stimulation in healthy individuals. J Neurol. *1993;240:373–376*.
14. Fleischmann A, Prolov K, Abarbanel J, Belmaker R H. The effect of transcranial magnetic stimulation of rat brain on behavioral models of depression. Brain Research. 1995;699:130–132.
15. Fleischmann A, Steppel J, Leon A, et al. The effect of transcranial magnetic stimulation compared with electroconvulsive shock on rat apomorphine induced stereotypy. Eur Neuropsychopharmacol. 1994;4:449–450.
16. Klein E, Ben-Shachar D, Grisaru N, Belmaker R H. Effects of rTMS on brain monoamines, receptors and animal models of depression. Presented to Biological Psychiatry; May, 1997, San Diego, Calif.
17. Epstein, C M, Schwartzberg D G, Davey K R, Sudderth D B, Localizing the site of magnetic brain stimulation in humans, *Neurology* 1990; 40:666–670.
18. Epstein C M, Lah J J, Meador K, Weissman J D, Gaitain L E, Dihenia B, Optimum stimulus parameters for lateralized suppression of speech with magnetic brain stimulation, *Neurology*, 47: 1590–1593 (December 1996).

The disclosures of all references cited in the present application are to be considered fully incorporated herein by reference.

Having described this invention with regard to specific embodiments, it is to be understood that the description is not meant as a limitation since further modifications may suggest themselves to those skilled in the art and it is intended to cover such modifications as fall within the scope of the appended claims.

I claim:

1. A transcranial magnetic stimulator comprising:
   (a) a core of highly saturable magnetic material, said highly saturable material comprising a magnetizable material which saturates at magnetic fields of at least 1.5 Tesla and said core being approximately hemispherical;
   (b) a stimulator coil for carrying electrical current in proximity to said core; and,
   (c) electric current means connected to said stimulator coil to create an electrical current flow in said stimulator coil and cause said stimulator coil and said core to generate a magnetic field.

2. A transcranial magnetic stimulator as claimed in claim 1, wherein said highly saturable material comprises vanadium permendur.

3. A transcranial magnetic stimulator as claimed in claim 1, wherein said highly saturable material comprises 3% grain oriented steel.

4. A transcranial magnetic stimulator as claimed in claim 1, wherein said core further comprises at least one generally semi-circular section.

5. A transcranial magnetic stimulator as claimed in claim 4, wherein said core further comprises generally triangular sections attached to each leg of said generally semi-circular section.

6. A transcranial magnetic stimulator as claimed in claim 5, wherein said generally triangular sections are integral with said generally semi-circular section.

7. A transcranial magnetic stimulator as claimed in claim 4, wherein said generally semi-circular section defines an arc of approximately two hundred eight (208) degrees.

8. A transcranial magnetic stimulator as claimed in claim 4, wherein said generally semi-circular section defines an arc of approximately two hundred five (205) degrees to two hundred fifteen (215) degrees.

9. A transcranial magnetic stimulator as claimed in claim 4, wherein said generally semi-circular section defines an arc of approximately one hundred ninety (190) degrees to two hundred thirty (230) degrees.

10. A transcranial magnetic nerve stimulator as claimed in claim 4, wherein said generally semi-circular section defines an arc of approximately one hundred eighty (180) degrees to two hundred seventy (270) degrees.

11. A transcranial magnetic stimulator as claimed in claim 1, wherein the shape of said core focuses and/or concentrates the magnetic field produced by said coil and said core.

12. A transcranial magnetic stimulator as claimed in claim 1 wherein said core is substantially tubular.

13. A transcranial magnetic stimulator as claimed in claim 12, wherein said core comprises at least one recess for holding said coil.

14. A transcranial magnetic stimulator as claimed in claim 1 further comprising a viewing port for proper positioning of said transcranial magnetic nerve stimulator.

15. A transcranial magnetic stimulator as claimed in claim 1 wherein said electric current means comprises:
  (a) a power supply;
  (b) a transformer connected to said power supply;
  (c) a full wave rectifier bridge connected to said transformer;
  (d) a diode connected to said full wave rectifier bridge;
  (e) capacitor means connected to said diode;
  (f) a thyristor connected to said capacitor, said thyristor connected to said stimulator coil; and
  (g) a second diode connected to said capacitor, said second diode also being connected to said stimulator coil.

16. A transcranial magnetic stimulator as claimed in claim 15, wherein said capacitor means comprises a single capacitor.

17. A transcranial magnetic stimulator as claimed in claim 1, wherein said core comprises a ribbon of said saturable material coated with a thin insulative coating.

18. A transcranial magnetic stimulator as claimed in claim 17, wherein said ribbon is further provided with an epoxy coating.

19. A transcranial magnetic stimulator as claimed in claim 18, wherein the ends of said core are smoothly ground.

20. A transcranial magnetic stimulator as claimed in claim 4, wherein said core further comprises at least two of generally semi-circular sections provided with a single coil wrapping around adjacent legs of said semi-circular sections.

21. A transcranial magnetic stimulator comprising:
  (a) an open core of highly saturable magnetic material, said highly saturable material comprising a material which saturates at magnetic fields of at least 1.5 Tesla;
  (b) a stimulator coil wrapped about said core for carrying electrical current in proximity to said core; and,
  (c) electric current means connected to said stimulator coil to create an electrical current flow in said stimulator coil and cause said stimulator coil and said core to generate a magnetic field.

22. A transcranial magnetic stimulator as claimed in claim 21, wherein said open core spans an angle of approximately between 205 to 215 degrees.

23. A transcranial magnetic stimulator as claimed in claim 21, wherein said open core spans an angle of approximately 208 degrees.

24. A transcranial magnetic stimulator as claimed in claim 21, wherein said highly saturable magnetic material saturates at magnetic fields of at least 2.0 Tesla.

25. A transcranial magnetic stimulator as claimed in claim 21, wherein said highly saturable material comprising vanadium permendur.

26. A transcranial magnetic stimulator as claimed in claim 21, wherein said highly saturable material comprising 3% grain oriented steel.

* * * * *